United States Patent
Acuña et al.

[11] Patent Number: 5,925,339
[45] Date of Patent: Jul. 20, 1999

[54] FRAGRANCE PRECURSOR COMPOUNDS FOR PREVENTING HUMAN MALODOR

[75] Inventors: Gonzalo Acuña, Dietikon; Georg Frater, Winterthur; Peter Gygax, Fällanden, all of Switzerland

[73] Assignee: Givaudan Roure SA, Vernier-Geneve, Switzerland

[21] Appl. No.: 08/879,239

[22] Filed: Jun. 19, 1997

[30] Foreign Application Priority Data

Jun. 24, 1996 [EP] European Pat. Off. .............. 96110149

[51] Int. Cl.$^6$ ............................. A61K 7/32; A61K 7/34; A61K 7/38

[52] U.S. Cl. ............................. 424/65; 424/66; 424/68; 424/DIG. 5; 554/101; 554/107; 560/158; 560/159; 560/160; 562/561; 562/563

[58] Field of Search .................................... 554/101, 107; 560/169, 159, 158; 562/561, 563; 424/65, 66, 68

[56] References Cited

U.S. PATENT DOCUMENTS

| | | | |
|---|---|---|---|
| 2,538,104 | 1/1951 | Koniuszy et al. | 560/169 X |
| 2,543,345 | 2/1951 | Waller et al. | 560/169 X |
| 2,762,841 | 9/1956 | Vassel | 562/563 |
| 2,846,469 | 8/1958 | Carron et al. | 562/563 |
| 3,979,449 | 9/1976 | Hirsbrunner et al. | 562/563 X |
| 4,111,933 | 9/1978 | Eckert et al. | 562/563 X |
| 4,721,803 | 1/1988 | Cesa et al. | 560/41 |
| 4,822,890 | 4/1989 | Bolin | 548/344 |
| 4,837,005 | 6/1989 | Brode et al. | 424/47 |
| 5,429,816 | 7/1995 | Hofrichter et al. | 424/66 |
| 5,514,654 | 5/1996 | Pecar et al. | 514/49 |
| 5,536,815 | 7/1996 | Carpino | 530/335 |
| 5,684,178 | 11/1997 | Philippe et al. | 560/169 |

FOREIGN PATENT DOCUMENTS

| | | | |
|---|---|---|---|
| 0 036 134 | 3/1981 | European Pat. Off. . | |
| 0 126 483 | 5/1984 | European Pat. Off. . | |
| 0466030 | 1/1992 | European Pat. Off. | 562/563 |
| 2021825 | 12/1971 | Germany | 560/169 |
| 90/03386 | 4/1990 | WIPO | 560/169 |
| 94/13624 | 6/1994 | WIPO | 560/169 |

*Primary Examiner*—Floyd D. Higel
*Attorney, Agent, or Firm*—Mark E. Waddell; Bryan Cave LLP

[57] ABSTRACT

The invention relates to agents preventing (the formation of) human malodor. In particular, the invention relates to the use of several classes of compounds which can act as such agents in cosmetic products, such as deodorants and antiperspirants. These compounds are normally odorless or nearly so, but upon contacting the skin as for example, in skin care compositions or in personal care compositions, they prevent malodor. The compounds under consideration are compounds of the formula $$X-(Z)_n-CO-NH-CH-(COO-Y)-CH_2CH_2CONH_2 \qquad I$$

The definition of the substituents is given in the specification.

5 Claims, No Drawings

FRAGRANCE PRECURSOR COMPOUNDS FOR PREVENTING HUMAN MALODOR

FIELD OF THE INVENTION

The invention relates to agents preventing (the formation of) human malodor. In particular, the invention relates to the use of several classes of compounds which can act as such agents in cosmetic products, such as deodorants and antiperspirants. These compounds are normally odorless or nearly so, but upon contacting the skin as for example, in skin care compositions or in personal care compositions, they prevent malodor.

SUMMARY OF THE INVENTION

The present invention now provides compounds which show a low level of odor, or are even odorless, prior to application to the skin, and which prevent, supress (the formation of) or attenuate malodor after application to the skin, in particular to the skin in the axilla. Fragrance precursor compositions and methods of using them are also described.

DETAILED DESCRIPTION

The compounds under consideration are compounds of the formula $$X-(Z)_n-CO-NH-CH-(COO-Y)-CH_2CH_2CONH_2 \quad I$$

wherein
X=alkyl, cycloalkyl, alkenyl, cycloalkenyl, aryl whereby each radical may also contain elements such as N, O, S, P, CO, and each of these radicals may be subsituted by groups, such as cycloalkyl, cycloalkenyl, aryl, hydroxy or acyloxy, e.g. alkanoyloxy, the radicals may further contain groups such as COOH, COOR$^1$, CN, CONHR$^2$
Y=H or X
Z=O or S
R$^1$ is alkyl, alkenyl, cycloalkyl
R$^2$ is alkyl or substituted alkyl, e.g. —CH(COOY)CH$_2$CH$_2$CONH$_2$
n=0,1
and, where,
n=0
X may also be NH$_2$, NHR$^1$, NR$_2^1$
and alkali, earth alkali, aluminium or, optionally substituted, ammonium salts of compounds, wherein Y=H.

Examples for the radicals X are:
Methyl,
ethyl,
propyl,
isopropyl,
tert.butyl,
sec.butyl,
isobutyl,
n-butyl,
pentyl,
hexyl,
heptyl,
octyl,
2-octyl,
nonyl,
2-nonyl,
decyl,
2-decyl,
undecyl,
2-undecyl,
dodecyl,
tridecyl,
tetradecyl,
pentadecyl,
hexadecyl,
heptadecyl,
octadecyl,
cyclopentyl,
cyclohexyl,
2-cyclohexylethyl,
2,6-dimethylheptyl,
geranyl,
neryl,
citronellyl,
9-decenyl,
2,6-dimethyl-5-heptenyl,
2,6-dimethyl-1,5-heptadienyl,
8,11-heptadecadienyl,
8-heptadecenyl,
cyclopentenyl,
cyclohexenyl,
phenyl,
p-methoxyphenyl,
benzyl,
2-phenylethyl,
1-phenylethyl,
2-(p-methoxyphenyl)-ethenyl,
3-(p-methylphenyl)-2-propyl,
3-(p-isopropylphenyl)-2-propyl,
3-(p-tert.butylphenyl)-2-propyl,
2,5,8-trioxanonyl,
acetonyl,
aminomethyl,
hydroxymethyl,
1-hydroxyethyl,
dimethylaminomethyl,
1-phenyl-1-aminoethyl,
carboxymethyl,
2-carboxyethyl,
3-carboxypropyl,
4-carboxybutyl,
5-carboxypentyl,
6-carboxyhexyl,
7-carboxyheptyl,
8-carboxyoctyl,
9-carboxynonyl,
10-carboxy-2,5,8-trioxanonyl,
7-carboxamido-5-carboxy-4-aza-3-oxo-heptyl,
8-carboxamido-6-carboxy-5-aza-4-oxo-octyl,
9-carboxamido-7-carboxy-6-aza-5-oxo-nonyl,
10-carboxamido-8-carboxy-7-aza-6-oxo-decyl,
11-carboxamido-9-carboxy-8-aza-7-oxo-undecyl,
14-carboxamido-12-carboxy-11-aza-10-oxo-tetradecyl, 2-pentyl-cyclopropyl,
menthyl,
terpineyl, etc.

The following known N-acylglutamines I are of particular importance:
N-formylglutamin
N-acetylglutamin
N-decanoylglutamin
N-undecanoylglutamin
N-dodecanoylglutamin
N-tetradecanoylglutamin
N-hexydecanoylglutamin
N-octadecanoylglutamin
N-phenylacetylglutamin
N-benzoylglutamin
N-carbonyloxymethylglutamin
N-carbonyloxyethylglutamin
N-tert.butoxycarbonylglutamin
N-carbonyloxybenzylglutamin
N-formylglutamin-benzylester
N-acetylglutamin-methylester
N-benzoylglutamin-methylester
N-carbonyloxybenzylglutamin-benzylester
N-acetylglutamin-aluminium-salt
N-carbamoylglutamin.

The following novel N-acylglutamines are also of particular importance:
N-2-methylheptanoylglutamin
N-10-undecenoylglutamin
N-3,7-dimethyl-6-octenoylglutamin
N-3,7-dimethyl-2,6-octadienoylglutamin
N-cinnamoylglutamin
N-3,6,9-trioxadecanoylglutamin
N-2-pentyl-cyclopropanoylglutamin
4-carbamoyl-2-(3-(3-carbamoyl-1-carboxypropylcarbamoyl)-propanoyl-amino)-butyric acid
4-carbamoyl-2-(4-(3-carbamoyl-1-carboxypropylcarbamoyl)-butanoylamino)-butyric acid
4-carbamoyl-2-(5-(3-carbamoyl-1-carboxypropylcarbamoyl)-pentanoyl-amino)-butyric acid
4-carbamoyl-2-(6-(3-carbamoyl-1-carboxypropylcarbamoyl)-hexanoyl-amino)-butyric acid
4-carbamoyl-2-(7-(3-carbamoyl-1-carboxypropylcarbamoyl)-heptanoyl-amino)-butyric acid
3-(3-carbamoyl-1-carboxypropylcarbamoyl)-propanoic acid
4-(3-carbamoyl-1-carboxypropylcarbamoyl)-butanoic acid
5-(3-carbamoyl-1-carboxypropylcarbamoyl)-pentanoic acid
6-(3-carbamoyl-1-carboxypropylcarbamoyl)-hexanoic acid
7-(3-carbamoyl-1-carboxypropylcarbamoyl)-heptanoic acid
4-carbamoyl-2-[2-(2-(2-[(3-carbamoyl-1-carboxypropylcarbamoyl)-methoxy]-ethoxy)-ethoxy)-acetylaminol]-butyric acid N-acetylglutamin-benzylester
N-acetylglutamin-dodecylester
N-acetylglutamin-tetradecylester
N-acetylglutamin-2-phenylethylester
N-acetylglutamin-geranylester
N-acetylglutamin-citronellylester
N-dodecanoylglutamin-2-phenylethylester
N-benzoylglutamin-phenylethylester
N-benzoylglutamin-benzylester
N-carbonyloxybenzylglutamin-geranylester
N-carbonyloxy-2-phenylethyl-glutamin-2-phenylethylester
N-acetylglutamin-sodium salt
N-acetylglutamin-potassium salt
N-dodecanoylglutamin-sodium salt
N-dodecanoylglutamin-potassium salt
N-dodecanoylglutamin-ammonium salt.

From this compilation it can be gathered, that a wide variety of compounds come into consideration. It can, for example, be seen that alkyl extends from $C_1$ to $C_{30}$ alkyl and alkenyl from $C_2$ to $C_{30}$ alkenyl, and one or more unsaturations may be present, and the respective chains may be linear or branched. Cycloalkyl and cycloalkenyl may extend from $C_3$ to $C_{12}$. Alkanoyloxy is preferably $C_{12-20}$-alkanoyloxy.

The aromatic rings encompass in particular, optionally substituted
one or more benzene rings
naphthalene.

The heterocycles encompass in particular, optionally substituted
pyridine
pyrrole
pyrrolidine
pyrimidine
furane
thiophene
tetrahydrofuran
quinoline
furanose
pyranose.

The compounds of formula I—or any mixture of such compounds—may preferably be used to prevent, suppress or attenuate undesirable odors, in particular human malodor, e.g. axillary malodor which is the result of bacterial degradation of primarily odorless substances present in apocrine sweat. This form of sweat is produced by the apocrine glands present in the skin of the underarm. Bacteria from the underarm region degrade some of the compounds present in the apocrine sweat resulting in the release of volatile compounds responsible for the characteristic axilla sweat malodor.

The compounds of formula I may preferably be used in consumer products, i.e. cosmetic products destined for application to human skin such as underarm deodorants or antiperspirants or other deodorants contacting the body, or in lotions, baby powders, baby lotions, ointments, foot products, body wipes, colognes, after-shave lotions, shaving creams, etc.

The compounds of formula I are virtually odorless under normal temperature and atmospheric conditions, i.e. about 10–50 degrees Celsius and about 20 to 100% relative humidity.

The compounds of formula I are not limited to any particular stereoisomers, all possible stereoisomers as well as racemates are thus included within the scope of formula I.

The compounds of formula I permit the development of methods useful in consumer products destined for attenuating or preventing human malodor. These compounds may be used individually in an amount effective to enhance this goal.

The amount required to produce the desired, overall effect varies depending upon the particular compounds of formula I chosen, the product in which it will be used, and the particular effect desired.

For example, depending upon the selection and concentration of the compound chosen, when added either singly or as a mixture e.g. to a deodorant composition at levels ranging from about 0.1 (or lower) to about 10% (or even higher) by weight, or most preferred about 0.25 to about 4% by weight formed composition serves to attenuate or to prevent the underarm odor, depending upon the selection and use levels of the compounds of formula I.

The compounds of formula I can accordingly be used in the manufacture of compositions used in the preparation of cosmetic products e.g. deodorants and antiperspirants, and as is evident from the above compilation, a broad range of known odorants or odorant mixtures can be used. In the manufacture of such compositions the known odorants or odorant mixtures set forth above can be used according to methods known to the perfumer, such as e.g. from W. A. Poucher, Perfumes, Cosmetics, Soaps, 2, 7th Edition, Chapman and Hall, London 1974.

To sum up, the present invention relates to:
1. A composition for application to human skin, containing a malodor preventing or malodor attenuating effective amount of at least one compound of the compound of formula I in a cosmetically acceptable carrier.
2. A cosmetic product e.g. a personal body deodorant or antiperspirant article, containing at least one compound I.
3. A method of suppressing human body malodor by means of compounds of the formula I, which comprises the application to human skin of a cosmetic product as defined above.
4. The use of a composition as defined above in a cosmetic product e.g. a personal body deodorant or antiperspirant composition.

The compounds of formula I can be prepared by using standard methods known to the skilled chemist. These standard methods can be found in the chemical literature.

N-acyl-glutamins or their esters can be prepared according to standard methods as described for example in Houben-Weyl, Methoden der Organischen Chemie, Synthese von Peptiden, Volume 15/1 p 46–305 (1974) by reaction of glutamin or glutamin esters with activated derivatives of carbonic or carboxylic acids. Activated derivatives are for example acid- or carbonic acid-halides, -anhydrides or activated esters such as N-hydroxybenzotriazinesters to name just one example. The base which may in some cases be indicated can be organic (Z. Grzonka, Synthesis 661 [1974]) or inorganic (O. Keller, Org. Synth. Coll. Vol. VII, 74 [1974] or P. Karrer, Helv. Chim. Acta 9 301 [1926]). Depending on each individual case, the reactions are conveniently run in organic aprotic solvents, in organic protic solvents or in mixtures of organic solvents with water or even in water. The temperature is usually in the range of −40° to 150° C., preferably −20° to 120° C.

N-Acylglutaminesters can also be prepared from N-acylglutamin by esterification methods, preferably those used in peptide chemistry. An example is the reaction of an appropriate halide with acylglutamin in the presence of a base. This base is preferably diazabicycloundecene (DBU) as, e.g. described by N. Ono, Bull. Chem. Soc. Jap. 51, 2401 (1978). In this case, the solvent is preferably aprotic, examples are hydrocarbons, ethers, esters or N-disubstituted amides, etc. The reaction temperature is preferably between 0° and 100° C.

Convenient methods are outlined in the Examples.

EXAMPLE 1

N-BOC-glutamin-benzylester 147 g N-BOC-glutamin (t-butyloxycarbonyl-glutamin), 77 g benzylchloride and 4 g benzylbromide were refluxed in 600 ml tetrahydrofuran for 2.5 hours in the presence of a 5% excess of diazabicycloundecene. After the removal of the solvent, the residue was taken up in water-ethylacetate and washed with citric acid, sodium bicarbonate and water. Evaporating of the solvent and recrystallization from ethylacetate-hexane gave 120 g white crystals. NMR (DMSO-$d_6$) among others: 7.36 (s,5H), 5.12 (dxd,2H), 3.989 (m,1H), 2.15 (t,2H), 1.38 (s,9H).

N-Lauroyl-glutamin (N-dodecanoyl-glutamin)

9.22 g lauroylchloride dissolved in 46 ml dioxane were slowly added to 6.72 g glutamine and 13.94 g trimethylamine in 92 ml water and 92 ml dioxane, the temperature being 0° C. After stirring at room temperature for 1 hour, the dioxane was evaporated and the remaining solution was acidified to pH 1 with HCl. The crystals were filtered off and recrystallized from acetone and then from methanol: 9.9 g white needles.

NMR (DMSO-$d_6$) among others: 8.05 (d,1H), 7.3 (s,1H), 6.78 (s,1H), 4.13 (m,1H), 2.03–2.18 (m,4H).

The following compounds were prepared according to the same procedure:

N-decanoyl-glutamin

N-tetradecanoyl-glutamin

N-hexadecanoyl-glutamin

N-octadecanoyl-glutamin

N-10-undecenoyl-glutamin 2-methylheptanoyl-glutamin.

EXAMPLE 2

N-tert.butyloxycarbonylglutamin 150 g di-tert.butyldicarbonate in 300 ml dioxane were added slowly at 0°C. to 100 g L-glutamin in 500 ml water and 207.5 g triethylamin. After stirring overnight, the organic solvents were removed and the residue was brought to pH 1 with conc. HCl. The aqueous phase was extracted several times with ethylacetate and the combined organic phases were then washed with water and brine before being evaporated. 147 g BOC-glutamine were obtained as a colorless glass.

N-benzyloxycarbonylglutamin was prepared according to the same procedure but using dibenzyl-dicarbonate as the reagent.

EXAMPLE 3

The following sets forth examples for the use of the Compounds of formula I in various products. The methods of forming the following compositions are well known to those skilled in the art. All formulations may contain additional ingredients known to those skilled in the art, e.g. colorants, opacifiers, buffers, antioxidants, vitamins, emulsifiers, UV absorbers, silicones and the like. All products can also be buffered to the desired pH.

All values are % w/w.

| Deo-colognes (four exemplary compositions): | | | | |
|---|---|---|---|---|
| Compound (I) | 0.5 | 1.5 | 2.5 | 6.0 |
| Fragrance | 0.5 | 1.5 | 2.5 | 6.0 |
| Triclosan (Ciba-Geigy) | 1.0 | — | 0.75 | 1.0 |
| Ethanol | 100 | 100 | 100 | 100 |

| Deo-Sticks: | |
|---|---|
| Antiperspirant stick | |
| Ethylene Glycol Monostearate | 7.0 |
| Shea butter | 3.0 |
| Neobee 1053 (PVO International) | 12.0 |
| Generol 122 (Henkel) | 5.0 |
| Kesscowax B (Akzo) | 17.0 |
| Dimethicone Dow Corning 345 | 35.0 |
| Aluminium Sesquichlorhydrate | 20.0 |
| Compound (I) | 0.5 |
| Fragrance | 0.5 |
| Antiperspirant stick | |
| Steary Alcohol | 17.0 |
| Castor Wax | 3.0 |
| Talc | 5.0 |
| Aluminum Zirconium Tetrachlorhydrate | 20.0 |
| Compound (I) | 1.0 |
| Fragrance | 1.0 |
| Dimethicone Dow 245 to | 100.0 |
| Clear Deodorant Stick | |
| Witconol APM | 43.0 |
| Propylene Glycol | 20.0 |
| Alcohol 39C | 20.0 |
| Water | 7.0 |
| Monamid 150ADD | 5.0 |
| Millithix 925 | 2.0 |
| Ottasept Extra | 0.5 |
| Compound (I) | 0.75 |
| Fragrance | 0.75 |
| Deodorant Stick | |
| Propylene Glycol | 69.0 |
| Water | 21.8 |
| Triclosan | 0.2 |
| Sodium Stearate | 8.0 |
| Compound (I) | 0.5 |
| Fragrance | 0.5 |
| Alcohol free Deodorant Stick | |
| Propylene Glycol-3 Myristyl Ether (Witconol APM) | 36.0 |
| Propylene Glycol | 36.0 |
| Water | 19.0 |
| Triclosan | 0.25 |
| Sodium Stearate | 7.75 |
| Compound (I) | 0.5 |
| Fragrance | 0.5 |
| Antiperspirant Aerosol | |
| Absolute Ethanol | 15.0 |
| Zirconium Aluminum tetrachlorhydrate | 5.0 |
| Bentone 38 | 1.5 |
| Compound (I) | 0.75 |
| Fragrance | 0.75 |
| S-31 Hydrocarbon propellant to | 100 |
| Antiperspirant Pump | |
| Water | 57.5 |
| Aluminum Sesquichlorhydrate | 20.0 |
| Triton X-102 (Union Carbide) | 2.0 |
| Dimethyl Isosorbide (ICI) | 20.0 |
| Compound (I) | 0.25 |
| Fragrance | 0.25 |

-continued

| Roll-On | |
|---|---|
| Dimethicone DC 354 (Dow Corning) | 69.0 |
| Bentone 38 | 10.0 |
| Rezal 36 GP (Reheis Chem. Co.) | 20.0 |
| Compound (I) | 0.5 |
| Fragrance | 0.5 |

In the above, the following components were used:

| | |
|---|---|
| Triclosan | 5-chloro-2-(2,4-dichlorophenoxy) phenol |
| Neobee 1053 | glycerol tricaprate/caprylate |
| Generol 122 | soya sterol |
| Kesscowax B | cetyl alcohol and glycol polymer |
| Witconol APM | polypropylene glycol-3 myristyl ether |
| Monamid 150ADD | cocoamide diethanolamine |
| Millithix 925 | dibenzylidene sorbitol |
| Ottasept Extra | quaternium 18 hectorite |
| Bentone 38 | quaternium 18 hectorite |
| Triton X-102 | octoxynol-13 |
| Dimethicone DC 354 | mixture of fully methylated linear siloxane polymers end-blocked with trimethylsiloxy units |
| Rezal 36 GP | aluminium zirconium tetrachlorohydrexglycine |

What is claimed is:

1. A composition for application to human skin, containing an amount effective to prevent, suppress or attenuate human malodor of at least one compound of the formula $$X-(Z)_n-CO-NH-CH-(COO-Y)-CH_2CH_2CONH_2$$

wherein

X=an alkyl, cycloalkyl, alkenyl, cycloalkenyl, or aryl substituent wherein each substituent contains at least one group selected from the group consisting of N, O, S, P, CO, and wherein each of these substituents contain at least one group selected from the group consisting of H, cycloalkyl, cycloalkenyl, aryl, hydrooxy or acyloxy, COOH, $COOR^2$, CN and $CONHR^2$, Y=H or X Z=0 or S $R^1$ is alkyl, alkenyl, cycloalkyl, $R^2$ is alkyl or substituted alkyl, n=0 or 1 and, where, when n=0,

X is $NH^2$, $NHR^1$, $NR^1$ and alkakli, earth alkali, aluminium or, unsubstituted or substituted ammonium salts of compounds, wherein Y=H, in a cosmetically acceptable carrier.

2. A composition according to claim 1, wherein the compound of formula I is selected from the group consisting of N-formylglutamin, N-acetylglutamin, N-decanoylglutamin, N-undecanoylglutamin, N-dodecanoylglutamin, N-tetradecanoylglutamin, N-hexydecanoylglutamin, N-octadecanoylglutamin, N-phenylacetylglutamin, N-benzoylglutamin, N-carbonyloxymethylglutamin,
N-carbonyloxyethylglutamin,
N-tert.butoxycarbonylglutamin,
N-carbonyloxybenzylglutamin,
N-formylglutamin-benzylester,
N-acetylglutamin-methylester,
N-benzoylglutamin-methylester,
N-carbonyloxybenzylglutamin-benzylester,
N-acetylglutamin-aluminium-salt,
N-2-methylheptanoylglutamin,
N-10-undecenoylglutamin,
N-3,7-dimethyl-6-octenoylglutamin,
N-3,7-dimethyl-2,6-octadienoylglutamin,
N-cinnamoylglutamin,
N-3,6,9-trioxadecanoylglutamin,
N-2-pentyl-cyclopropanoylglutamin,
N-benzyloxy-carbonylglutamin,
N-tert.butyloxycarbonylglutamin-benzyl ester,
4-carbamoyl-2-(3-(3-carbamoyl-1-carboxypropylcarbamoyl)-propanoyl-amino)-butyric acid,
4-carbamoyl-2-(4-(3-carbamoyl-1-carboxypropylcarbamoyl)-butanoylamino)-butyric acid,
4-carbamoyl-2-(5-(3-carbamoyl-1-carboxypropylcarbamoyl)-pentanoyl-amino)-butyric acid,
4-carbamoyl-2-(6-(3-carbamoyl-1-carboxypropylcarbamoyl)-hexanoyl-amino)-butyric acid,
4-carbamoyl-2-(7-(3-carbamoyl-1-carboxypropylcarbamoyl)-heptanoyl-amino)-butyric acid,
3-(3-carbamoyl-1-carboxypropylcarbamoyl)-propanoic acid,
4-(3-carbamoyl-1-carboxypropylcarbamoyl)-butanoic acid,
5-(3-carbamoyl-1-carboxypropylcarbamoyl)-pentanoic acid,
6-(3-carbamoyl-1-carboxypropylcarbamoyl)-hexanoic acid,
7-(3-carbamoyl-1-carboxypropylcarbamoyl)-heptanoic acid,
4-carbamoyl-2-[2-(2-(2-[(3-carbamoyl-1-carboxypropylcarbamoyl)-methoxy]-ethoxy)-ethoxy)-acetylamino]-butyric acid,
N-acetylglutamin-benzylester,
N-acetylglutamin-dodecylester,
N-acetylglutamin-tetradecylester,
N-acetylglutamin-2-phenylethyl ester,
N-acetylglutamin-geranylester,
N-acetylglutamin-citronellylester,
N-dodecanoylglutamin-2-phenylethylester,
N-benzoylglutamin-phenylethylester,
N-benzoylglutamin-benzylester,
N-carbonyloxybenzylglutamin-geranylester,
N-carbonyloxy-2-phenylethyl-glutamin-2-phenylethylester,
N-acetylglutamin-sodium and -potassium salt,
N-dodecanoylglutamin-sodium, -potassium and -ammonium salt, and
N-carbamoylglutamin.

3. A cosmetic product comprising at least one compound I as defined in claim 1.

4. A method of preventing, suppressing or attenuating human body malodor comprising applying to human skin at least one of the compounds of formula I as defined in claim 1 in the form of a cosmetic product as defined in claim 3.

5. A composition comprising at least one of the compounds of formula I as defined in claim 1 for application to human skin.

* * * * *